United States Patent
Teggatz et al.

(10) Patent No.: US 8,408,900 B2
(45) Date of Patent: Apr. 2, 2013

(54) ELECTROCHEMICAL DISPENSING APPARATUS AND METHOD

(75) Inventors: Ross Teggatz, McKinney, TX (US); Wayne Chen, McKinney, TX (US)

(73) Assignee: Triune IP LLC, Richardson, TX (US)

( * ) Notice: Subject to any disclaimer, the term of this patent is extended or adjusted under 35 U.S.C. 154(b) by 134 days.

(21) Appl. No.: 12/832,519

(22) Filed: Jul. 8, 2010

(65) Prior Publication Data
US 2011/0008744 A1    Jan. 13, 2011

Related U.S. Application Data

(60) Provisional application No. 61/223,934, filed on Jul. 8, 2009.

(51) Int. Cl.
*A61C 17/00* (2006.01)
(52) U.S. Cl. .......................................................... 433/80
(58) Field of Classification Search .................. 433/1, 6, 433/24, 29, 32, 80, 87–90, 215–217.1; 604/20; 205/619; 204/229.4, 229.7; 422/186, 186.03, 422/186.04
See application file for complete search history.

(56) References Cited

U.S. PATENT DOCUMENTS

| | | | | |
|---|---|---|---|---|
| 4,376,628 A * | 3/1983 | Aardse | .............................. | 433/80 |
| 6,135,126 A * | 10/2000 | Joshi | .............................. | 132/308 |
| 7,003,353 B1 * | 2/2006 | Parkhouse | ........................ | 607/45 |
| 2005/0224366 A1 * | 10/2005 | Hodgson et al. | .............. | 205/619 |
| 2006/0052768 A1 * | 3/2006 | Joshi et al. | .................. | 604/892.1 |
| 2006/0283465 A1 * | 12/2006 | Nickel et al. | .................. | 128/898 |
| 2007/0154863 A1 * | 7/2007 | Cai et al. | .......................... | 433/89 |
| 2008/0257915 A1 * | 10/2008 | Wold | .............................. | 222/389 |

* cited by examiner

*Primary Examiner* — Yogesh Patel
(74) *Attorney, Agent, or Firm* — Jackson Walker L.L.P.; Christopher J. Rourk

(57) ABSTRACT

The disclosed invention provides electrochemical dispensing apparatus. According to the principles of the invention, a microelectronic electrochemical dispenser is used to cause the release of one or more selected chemical substance from a stored chemical compound. The release is controlled using a timer or sensor apparatus in a controlling device, preferably an ASIC.

18 Claims, 3 Drawing Sheets

ELECTROCHEMICAL DISPENSING APPARATUS AND METHOD

PRIORITY ENTITLEMENT

This application is entitled to priority based on Provisional Patent Application Ser. No. 61/223,934 filed on Jul. 8, 2009. This application and the Provisional patent application have at least one common inventor.

TECHNICAL FIELD

The invention relates to electronic circuits. More particularly, the invention relates to electronic circuits configured for the release of selected chemicals.

BACKGROUND OF THE INVENTION

There are various situations in which it is desirable to apply a chemical element or chemical compound in a relatively small, focused area according to a timed schedule or in dynamic response to particular conditions. In the medical field, for example, the timed or responsive release of medication or treatment such as the application of fluoride in dentistry is known to be beneficial. Periodic or responsive renewal of lubricants for micromechanical devices is another application in which the dispensation of relatively small amounts of selected compounds may be used to advantage. Returning to the example presented by the field of dentistry, oral biofilms are causative agents in many biological processes such as dental caries (cavities), periodontal disease and perio-implantitis. Dental biofilms contains a diverse species of microbes some of which have been identified as etiological agents for systemic diseases. The accumulation of dental biofilm can instigate a subsequent inflammatory and immune response. The control of dental biofilm is of paramount importance in managing periodontal disease and also plays a key role in disrupting the caries process. The human oral cavity has in excess of 700 different types of aerobic and anaerobic bacteria species. Biofilms are a complex community of microorganisms characterized by the excretion of a protective extracellular matrix, glycocalix, within which microbes are embedded. This matrix is adhesive in quality and allows for the attachment of microbe to microbe. The microbes in biofilms have a high rate of reproduction and are physiologically adaptive. As the microbes reproduce, they form complex, compound, interdependent colonies and the biofilms can achieve considerable thickness, up to 1 mm thickness within a four day period if undisturbed. Oral biofilms are initially colonized by gram-positive aerobic bacteria. As the biofilm becomes more mature and thickness increases, gram-negative anaerobic bacteria prevail and dominate. Infection with gram-negative anaerobes is associated with the release of bacterial toxins and proteolytic enzymes which are virulent, cytotoxic, or irritating to host tissues, resulting in host tissue injury and inflammation. The effect on the host is dependent upon the vulnerability of the host, the presence and prevalence of pathogenic bacteria as well as that of protective bacteria. In periodontal disease, relapse or refractory cases are intimately related to the presence of residual biofilm. Bacteria growing in biofilms have increased tolerance and resistance to antibiotics and antimicrobial agents, including those used in dentifrices and mouthwashes. The surface of the biofilm appears to be a physical barrier to the efficacy of chlorhexidine, inhibiting penetration or extinguishing it.

In spite of efforts to the contrary, dental Caries remains an endemic problem worldwide. Despite some modest decreases in tooth decay in the overall population, the incidence of decay remains high in specific subgroups. In particular, this includes individuals from low socioeconomic backgrounds and immigrant, ethnic minority populations. Cariogenic bacteria are passed on by caregivers (mothers) at a young age, the median age being 26 months. Early childhood caries affects one in six children. By the first grade, 50% of all children in the USA have had tooth decay. Early childhood caries appears to predispose children for decay throughout their lives. The implementation of water fluoridation has been extremely beneficial, but it is not without limitations. Although water fluoridation does affect the fluoride content of enamel during tooth development, the benefit of water fluoridation is primarily topical as opposed to intrinsic fluoride incorporation during tooth development. Fluoride reduces tooth decay by assisting in the prevention of demineralization and by remineralizing incipient lesions. Tooth decay is a process whereby demineralization, the mineral transfer from the tooth to the surrounding surface, is balanced or counteracted by remineralization. As a result, vast potential exists for improving and augmenting presently existing intervention techniques.

In the micromechanical field, lubrication in MEMs devices can be problematic. Traditional oils are generally not used because their molecules are too large in relation to the surfaces to be lubricated. Solid lubricants, such as various carbon compounds and monolayers of fluorocarbon materials may be used, but are susceptible to wear and are not self-renewing. Due to the foregoing and possibly additional problems, improved apparatus and methods for preventing tooth demineralization and promoting remineralization would be a useful contribution to the arts. In a broader sense, the electrochemical dispensing of targeted chemicals from chemical compounds would provide one or more advantages in diverse applications, such as in the medical and micromechanical fields.

SUMMARY OF THE INVENTION

In carrying out the principles of the present invention, in accordance with preferred embodiments, the invention provides advances in the arts with useful and novel apparatus for electronically controlled chemical dispensation in target locations. Embodiments described herein preferably include ASIC devices for dispensing selected chemicals containing the element fluorine in an oral environment. The embodiments described herein are intended to be exemplary and not exclusive. Variations in the practice of the invention are possible and preferred embodiments are illustrated and described for the purposes of clarifying the invention. All possible variations within the scope of the invention cannot, and need not, be shown.

According to one aspect of the invention, in an example of a preferred embodiment, a microsystem for controlling the release of a target chemical from a chemical compound through an electrochemical reaction is provided. The microsystem includes a chemical compound formulated to ensure the availability of a selected target chemical. A controlling mechanism is electrically connected with the chemical compound for promoting an electrochemical reaction in order to cause the release of the target chemical.

According to another aspect of the invention, preferred embodiments of the invention described herein include an application specific integrated circuit (ASIC).

According to another aspect of the invention, a microsystem for controlling the release of a target chemical from a chemical compound through an electrochemical reaction further includes a rechargeable battery.

According to another aspect of the invention, preferred embodiments are equipped with compounds including the element fluorine.

According to yet another aspect of the invention, a microsystem for controlling the release of a target chemical from a chemical compound through an electrochemical reaction further includes both a rechargeable battery and an energy harvesting circuit connected with an ASIC.

According to yet another aspect of the invention, a preferred microsystem for releasing a selected chemical substance provides a chemical compound selected for its capacity to release the selected chemical substance upon electrical stimulation. A power source and an ASIC are furnished for causing electrical stimulation in order to cause the release of the selected chemical substance from the compound.

The invention has advantages including but not limited to providing one or more of the following features. In the exemplary preferred embodiment used for dispensing fluoride, calcium, or phosphate adjacent to teeth, by affecting the concentration gradient of these minerals, the tooth-decay process can be disrupted. The solution lies within reducing the mineral transfer out of the tooth and promoting the mineral transfer into the tooth. When fluoride is applied, spherules of calcium fluoride are formed on the tooth surface. Following acid attacks, calcium, phosphate, and fluoride are released from these mineral reservoir-like spherules, inhibiting demineralization and initiating remineralization. It is believed that a higher concentration of topical fluoride coupled with a more prolonged application result in a greater release of fluoride from the agent, in addition of the deposition and access to these spherules. Increasing the available levels of calcium and fluoride has been shown to increase available fluoride. The elevated mineral concentration advantageously diminishes the loss of minerals at the tooth surface and hence reduces the possibility for demineralization. It is believed that lubricated surfaces of MEMs devices can be renewed in a similar manner using the techniques and apparatus of the invention. These and other advantages, features, and benefits of the invention can be understood by one of ordinary skill in the arts upon careful consideration of the detailed description of representative embodiments of the invention in connection with the accompanying drawings.

BRIEF DESCRIPTION OF THE DRAWINGS

The present invention will be more clearly understood from consideration of the description and drawings in which.

References in the detailed description correspond to like references in the various drawings unless otherwise noted. Descriptive and directional terms used in the written description such as front, back, top, bottom, upper, side, et cetera; refer to the drawings themselves as laid out on the paper and not to physical limitations of the invention unless specifically noted. The drawings are not to scale, and some features of embodiments shown and discussed are simplified or amplified for illustrating principles and features as well as advantages of the invention.

DESCRIPTION OF PREFERRED EMBODIMENTS

While the making and using of various exemplary embodiments of the invention are discussed herein, it should be appreciated that the apparatus and techniques for its use exemplify inventive concepts which can be embodied in a wide variety of specific contexts. It should be understood that the invention may be practiced in various applications and embodiments without altering the principles of the invention. For purposes of clarity, detailed descriptions of functions, components, and systems familiar to those skilled in the applicable arts are not included. In general, the invention provides devices for the dispensing of selected chemicals at target locations using electronically controlled electrochemical reactions. The invention is described in the context of representative example embodiments. Although variations and alternatives for the details of the embodiments are possible, each has one or more advantages over the prior art.

Figure 1:
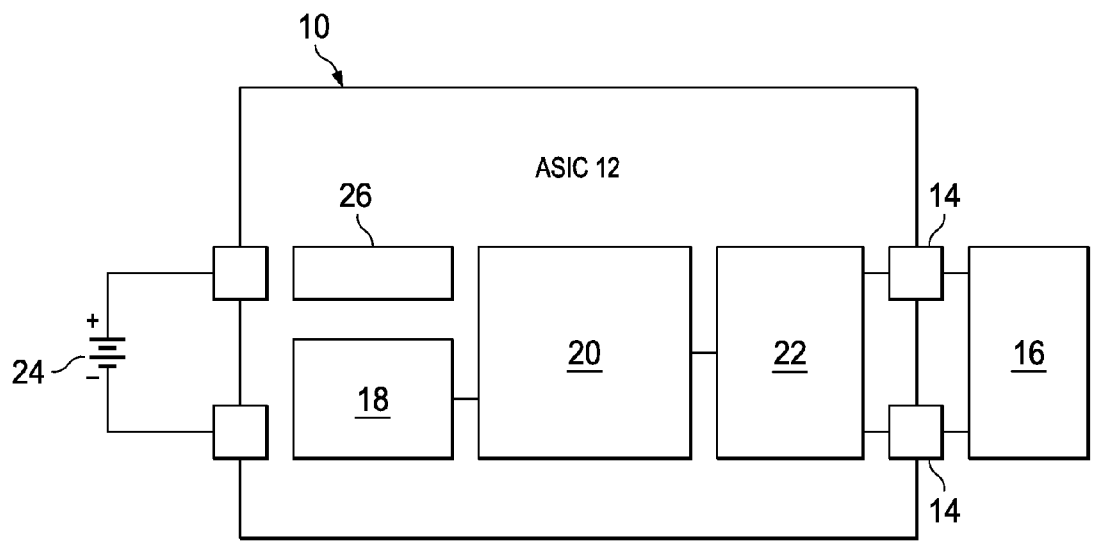
FIG. 1 is a simplified schematic diagram illustrating examples of preferred embodiments of electrochemical devices.

In an example of a preferred embodiment of the invention, an implanted electrochemical dispensing apparatus may be used to provide a constant source of fluoride to minimize or eliminate enamel decay of a damaged tooth. This appliance can be placed within a crown or filling, bonding onto the side of a tooth, or placed within a removable appliance such as a mouth piece or retainer. Using an electro-chemical reaction, and controlling the timing and rate of release of the fluoride, the enamel of the tooth may strengthened and protected. A schematic block diagram of one preferred implementation for an electrochemical dispensing apparatus is shown in FIG. 1. Apparatus 10 is shown to include an application specific integrated circuit (ASIC) 12. The ASIC 12 is preferably provided in order to control the release of the fluoride 14 from the chemical compound 16 according to preselected criteria. Fluoride-containing compounds that may be used include, sodium fluoride, stannous fluoride, and monofluorophosphate, for example. Provided within the ASIC 12, an oscillator and timer circuit 18 is used to clock a state machine 20, and also provide a time base for controlling the release of the fluoride 14 from the fluoride-based chemical compound 16. When fluoride release is required, as indicated by the timer 18, or by an optional sensor, not shown, the electrochemical driver circuit 22 in the ASIC is activated and a current is provided to the fluoride-based chemical compound 16, thereby releasing the fluoride 14, causing its dispersal, in this case adjacent to the enamel of a selected tooth or teeth. Power to the ASIC 12 is preferably supplied with a battery 24. Preferably, embodiments of this system 10 may also include an energy harvesting element 26 to replenish a rechargeable battery 24. The charging element may be omitted in some embodiments as well. The energy from the energy harvesting element 26 is conditioned by the ASIC 12 before it is stored on the rechargeable battery 24. The harvested energy may come from several sources, such as inductive charger or a MEMs (microelectromechanical) system charging device, to cite two examples.

Without departing from the principles of the invention, alternative implementations of an electrochemical dispensing apparatus may omit the battery, replacing it with an alternative charge storage device such as a capacitor, which is charged through inductive charging, RF (radio frequency) energy or other types of energy harvesting techniques. This may assist in minimizing the overall profile of the apparatus.

In addition to, or instead of releasing fluoride, other compounds beneficial to the target, e.g., tooth enamel or MEMs surfaces, could be utilized. Also, the system may provide sensing capabilities such as those suitable for identifying biofilm conditions by measuring pH content and/or fluctuations in pH content over time, and control the release of chemical compounds based upon dynamically sensed conditions. Other parameters which may be measured include alkalinity, temperature, resistivity, and the like. Optionally, information relating to the environmental changes in the operating environment may be stored over time. This stored data may be used to provide long-term and real-time information to correlate environmental conditions and chemical dispersal events within the operating environment, e.g., in the mouth cavity. Such data may be stored within the ASIC through the use of memory devices, or placed in a cache device, and then transmitted to an external device for storage and/or further processing or use.

Figure 2:
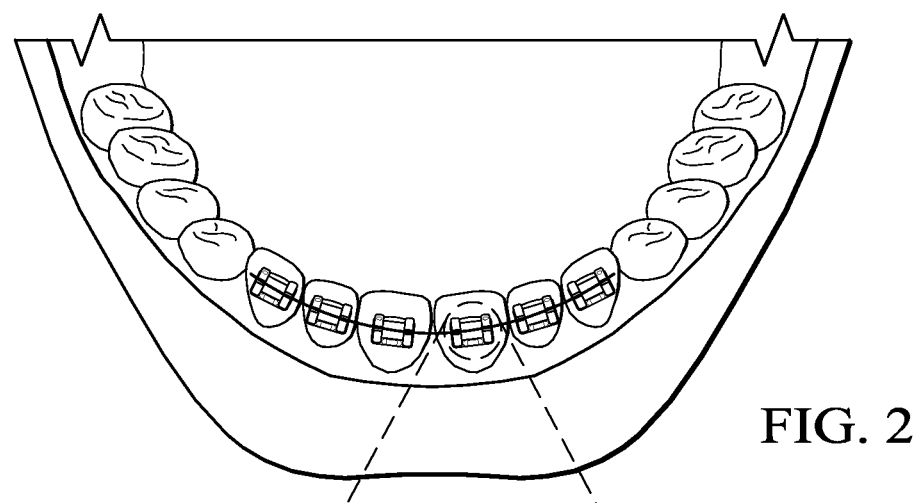
FIG. 2 is a simplified diagram illustrating an example of the use of preferred embodiments of electrochemical devices.
Figure 2:
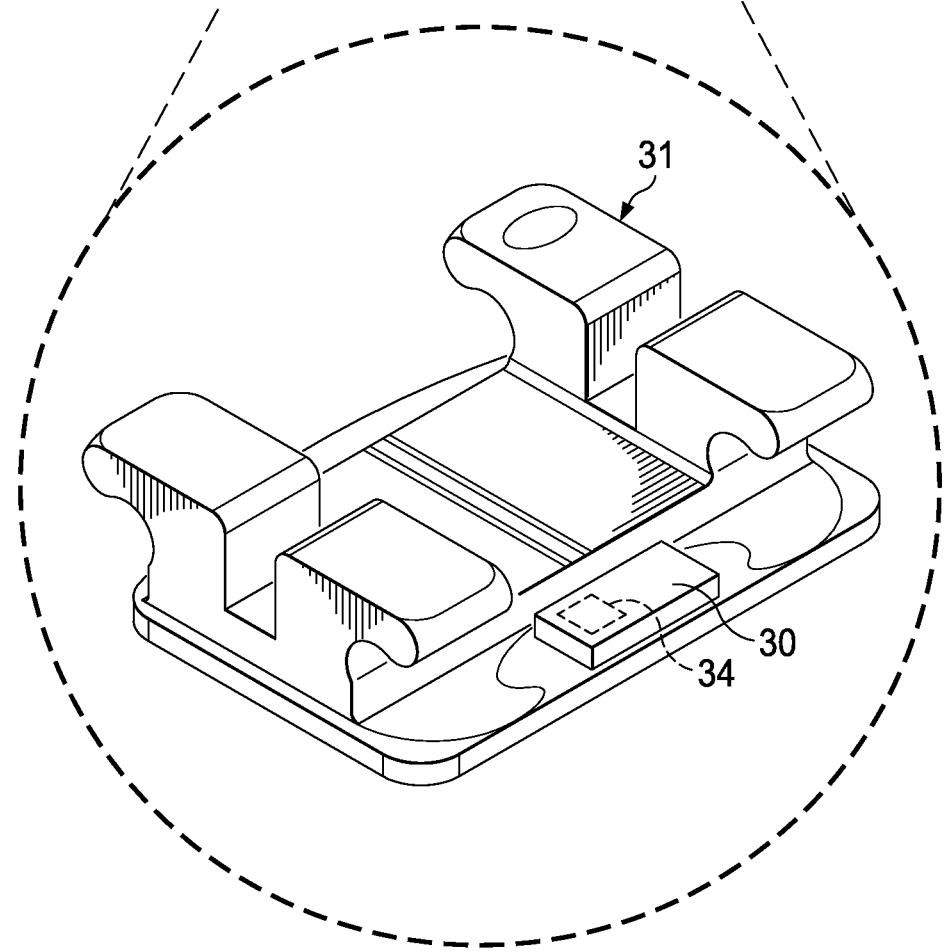
Figure 3:
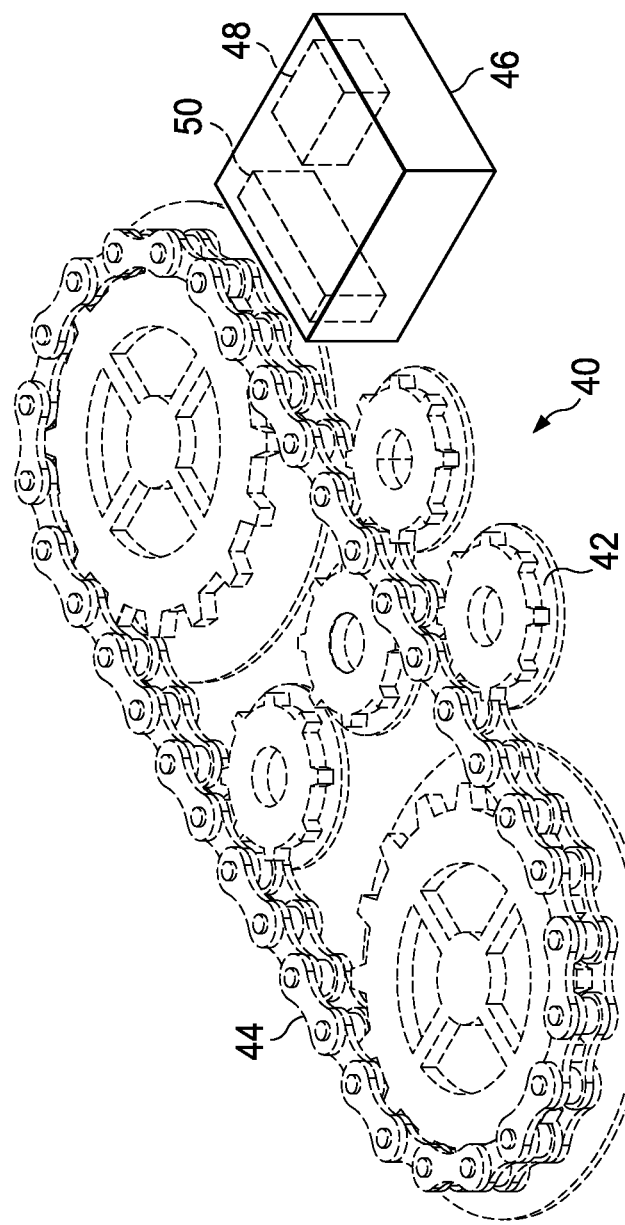
FIG. 3 is a simplified diagram illustrating an alternative example of the use of preferred embodiments of electrochemical devices.

Now referring primarily to FIG. 2, and example of the deployment of an electrochemical dispensing apparatus 30 according to a preferred embodiment of the invention is shown in the context of a dental application. As shown, an electrochemical dispensing apparatus, such as a bracket 31 for orthodontic braces 32, may be equipped with an electrochemical dispensing apparatus 30. As described above with reference to FIG. 1, the electrochemical dispensing apparatus 30 contains one or more chemical compounds selected for their ability to release fluoride upon electrical stimulation. Based upon a control program in an ASIC 34 of the electrochemical dispensing apparatus 30, the fluoride may be dispersed in close proximity to the targeted tooth, or teeth. Although the example of the preferred embodiment shown and described relates to a specific dental application where the invention may be used, it should be apparent to those skilled in the relevant arts that the principles of the invention may be practiced in various applications throughout the dental, medical, chemical, and mechanical fields. Another example of a preferred embodiment of the invention is depicted in FIG. 3. As shown, MEMs apparatus 40 may include several movable surfaces that come in contact with one another, e.g., 42, 44, for which lubrication may be necessary or desirable. An electrochemical dispensing apparatus 46 configured for dispensing lubricant is positioned in close proximity to the selected surfaces, 42, 44. The electrochemical dispensing apparatus 46 is preferably equipped with an ASIC 48 and a suitable reservoir or staging area 50 for retaining a chemical compound selected for its ability to release one or more suitable lubricants, such as fluorine-bearing compounds, silanes, or fluorine-bearing ionic fluids, for example. The ASIC 48 may be programmed with instructions for initiating the dispensing of lubricant based on elapsed time, usage time of associated MEMs apparatus, or environmental conditions such as temperature, or other parameters.

The electrochemical dispensing devices of the invention provide one or more advantages including but not limited to targeted, controlled, chemical dispensing useful in dental, medical, and small- and micro-mechanical applications and possibly other applications. While the invention has been described with reference to certain illustrative embodiments, those described herein are not intended to be construed in a limiting sense. For example, variations or combinations of features or materials in the embodiments shown and described may be used in particular cases without departure from the invention. Although the presently preferred embodiments are described herein in terms of particular examples, modifications and combinations of the illustrative embodiments as well as other advantages and embodiments of the invention will be apparent to persons skilled in the arts upon reference to the drawings, description, and claims.

We claim:

1. A dental bracket system comprising:
a bracket;
an electrochemical dispensing unit disposed on the bracket, said electrochemical dispensing unit comprising an application specific integrated circuit and a reservoir; said application specific integrated circuit comprises a controlling mechanism and an electrochemical driver circuit;
a chemical compound disposed within the reservoir and formulated to ensure availability of a selected target chemical; and
the controlling mechanism and the electrochemical driver circuit of the integrated circuit electrically connected to the reservoir for promoting an electrochemical reaction for causing a release of the target chemical.

2. The system according to claim 1 wherein the chemical compound further comprises fluoride.

3. The system according to claim 1 wherein the chemical compound further comprises sodium fluoride.

4. The system according to claim 1 wherein the chemical compound further comprises stannous fluoride.

5. The system according to claim 1 wherein the chemical compound further comprises sodium monofluorophosphate.

6. The system according to claim 1 wherein the chemical compound further comprises a silane.

7. The system according to claim 1 wherein the chemical compound further comprises an ionic fluid.

8. The system according to claim 1 wherein the chemical compound further comprises a fluorine-bearing silane.

9. The system according to claim 1 wherein the target chemical further comprises fluorine.

10. The system according to claim 1 wherein the chemical compound further comprises carbon.

11. The system according to claim 1 wherein the chemical compound further comprises hydrogen.

12. The system according to claim 1 wherein the chemical compound further comprises argon.

13. The system according to claim 1 wherein the application specific integrated circuit further comprises a timer circuit for controlling the operation of the application specific integrated circuit.

14. The system according to claim 1 further comprising a rechargeable battery operably coupled for promoting the electrochemical reaction.

15. The system according to claim 1 further comprising an energy harvesting circuit operably coupled to the application specific integrated circuit.

16. The system according to claim 1 wherein the application specific integrated circuit is operably coupled to a microelectromechanical energy harvesting device.

17. The system according to claim 1 wherein the application specific integrated circuit is operably coupled to an inductive energy harvesting device.

18. The system according to claim 1 wherein the application specific integrated circuit is configured for acquiring data for use in controlling the operation of the application specific integrated circuit.

* * * * *